United States Patent [19]

Proulx

[11] Patent Number: 4,920,962
[45] Date of Patent: May 1, 1990

[54] SPLINT-LIKE ELEMENT FOR USE IN END-TO-END NERVE SUTURE

[76] Inventor: Claude Proulx, 1580 Francheville, Montreal, Quebec, Canada, H2C 1X6

[21] Appl. No.: 275,458

[22] Filed: Nov. 23, 1988

[51] Int. Cl.[5] ............................................. A61B 17/04
[52] U.S. Cl. .................................................. 606/152
[58] Field of Search ......................... 128/334 R, 335.5

[56] References Cited

U.S. PATENT DOCUMENTS 4,632,113  12/1986  Ablaza ............................. 128/335.5

OTHER PUBLICATIONS

"Management of Peripheral Nerve Problems", chapters 20 and 26, George E. Omer Jr. et al., W. B. Sauhders Co. 1980.

Primary Examiner—Edward M. Coven
Assistant Examiner—Gary Jackson
Attorney, Agent, or Firm—Edwin E. Greigg

[57] ABSTRACT

Disclosed is a splint-like element for use in end-to-end nerve suture to eliminate tension at the anastomosis site and thus allow optimal coaptation between the nerve ends to be sutured. The element comprises an elongated body made of a material that is rigid and slightly resilient and is biologically acceptable, such as silicone. The body is long enough to have one end attachable to the epineurium of one of the nerve ends by at least one but preferably two longitudinally spaced-apart sutures, and another end attachable to the epineurium of the other nerve end also by at least one but preferably two other longitudinally spaced-apart sutures. The element also comprises pieces of reinforcing material preferably consisting of beads of plastic material embedded into the body material wherever this body is intended to be attached to the epineurium to prevent the body material from being torn or otherwise cut by the sutures. In use, two such splint-like elements may be attached symmetrically to the epineurium of the nerve ends while the same are held into contact in order to make the suture site tension free. Then, the nerve ends may be sutured as is known in the medical art to achieve the requested anastomosis.

17 Claims, 2 Drawing Sheets

SPLINT-LIKE ELEMENT FOR USE IN END-TO-END NERVE SUTURE

BACKGROUND OF THE INVENTION (a) Field of the Invention

The present invention relates to a stent or splint-like element for use in end-to-end nerve suture to eliminate tension at the anastomosis site and thus allow optimal coaptation between the nerve ends to be sutured.

The invention also relates to a method of carrying out end-to-end nerve suture, using such stent or splint-like elements to achieve maximum coaptation between the nerve ends.

The terms stent and splint-like are of the same meaning and may be interchanged hereafter.

(b) Description of the Prior Art

There are presently numerous techniques for use in nerve repairs, and more particularly for use in end-to-end nerve sutures.

Over the last decades, numerous improvements have been made to these techniques, in order, for example, to prevent irritation from the suture material, to achieve good coaptation of the nerve endings, to achieve bridging of nerve gaps with nerve grafts, to prevent stray regenerating nerve fibers and/or growth of fibrous scars, etc.

However, very few studies and suggestions have been made up to now in order to solve the major problem encountered by those practicing end-to-end nerve sutures, namely to eliminate tension at the anastomosis site.

By way of example, it is known that the suture technique known as "plasma clot method" and commonly used to perform sutureless nerve repair, cannot be carried out when there is tension at the suture site. With such a method, when there is some tension, coaptation cannot be achieved and nerve grafting is required.

It is also known that the technique known as "adhesive microanastomosis", which technique is carried out with an adhesive such as FIBRINE® or HISTOACRYL®, cannot also be employed for nerve sutures when there is tension.

It is further known that most of the other existing techniques such as those known as "tubular splicing", "epineurial cuff neurorrhapy" or laser microanastomosis, are also very difficult to perform under tension.

It is therefore apparent that tension is and has always been a very important problem in nerve suture especially when considering that some degree of defect always exists between two nerve ends and that accordingly, it is almost impossible to avoid tension at the anastomosis site while matching the fasciculi.

To solve this problem, it has already been suggested to use very fine metal wire tension sutures. This technique however has proved not to be really satisfactory as such metal wires, that are rather big, can only be used to suture the adjacent lips of the epineurium of the nerve ends.

Since it is, in practice, almost impossible to achieve proper anastomosis under nerve tension, interfascicular nerve graft must usually be carried out to make it sure that there is no tension at the time of suturing the nerve ends. The results with nerve grafting however are always less than with nerve anastomosis is under no tension, because the graft nerve has to survive and the axons have to pass two anastomosis sites. Moreover, the amount of nerves to be used for such grafting is, in practice, limited.

Another technique to eliminate tension has been suggested by K. TSUGE et al under the name of "anchoring funicular sutures" (see K. TSUGE et al, Plast. Reconst. Surg., 56:496, 1975). This technique makes use of a needle fitted with a looped suture wire deviced for tendon suture. Basically, this technique consists of attaching the wire to the epineurium of one nerve end, then passing it through the epineurium of both nerve ends and subsequently tightening it and attaching it to the epineurium of the other nerve end in such a manner as to make to anastomosis site tension free.

SUMMARY OF THE INVENTION

A first object of the present invention is to provide a new surgical tool, namely a splint-like element, for use in end-to-end nerve suture to eliminate tension between the nerve ends at the anastomosis site and thus allow optimal coaptation between these ends.

Another object of the invention is to provide a method very simple to be carried out to perform end-to-end nerve suture, using splint-like elements of the above mentioned type to achieve maximum coaptation between the nerve ends.

A further object of the invention is to also provide such a method of carrying out end-to-end nerve suture which, due to a complete elimination of the tension at the end of the anastomosis site, makes it possible to avoid nerve grafting.

In accordance with the invention, the above mentioned objects are achieved with a splint-like element for use in end-to-end nerve suture to eliminate tension at anastomosis site and thus allow optimal coaptation between the nerve ends to be sutured, which element comprises an elongated body made of a material that is rigid or slightly resilient and is biologically acceptable, such as silicone. The body is long enough to have one end attachable to the epineurium of one of the nerve ends by at least one but preferably two longitudinally spaced-apart sutures, and another end attachable to the epineurium of the other nerve end also by at least one but preferably two other longitudinally spaced-apart sutures. The element also comprises pieces of reinforcing material preferably consisting of beads of plastic material embedded into the body material wherever this body is intended to be attached to the epineurium to prevent the body material from being torn or otherwise cut by the sutures. In use, two such splint-like elements may be attached symmetrically to the epineurium of the nerve ends while the same are held in contact in order to make the suture site tension free. Then, the nerve ends may be sutured as is known in the medical art to achieve the desired anastomosis.

BRIEF DESCRIPTION OF THE DRAWINGS

The invention and its numerous advantages will be better understood upon reading of the following non restrictive description of a preferred embodiment thereof, made with reference to the accompanying drawings in which.

DESCRIPTION OF A PREFERRED EMBODIMENT OF THE INVENTION

Figure 1:
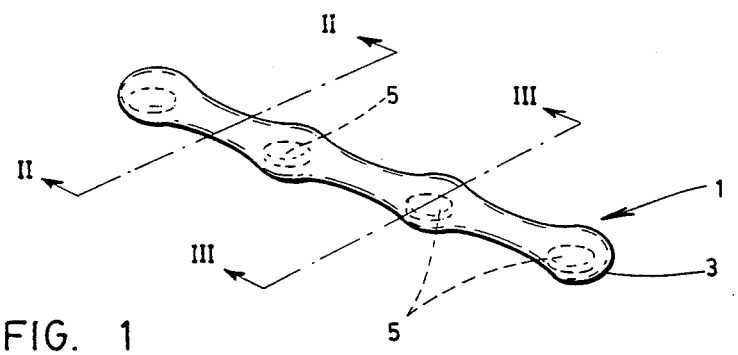
FIG. 1 is a perspective view of a splint-like element according to the invention for use in end-to-end nerve suture.
Figure 3:
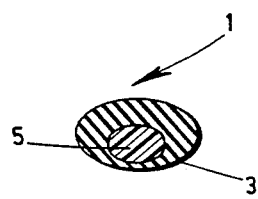
FIG. 3 is a cross-sectional view of the element shown in FIG. 1, taken along line III—III thereof.
Figure 2:
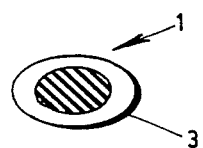
FIG. 2 is a cross-sectional view of the element shown in FIG. 1, taken along line II—II thereof.

The splint-like element 1 as shown in FIGS. 1 to 3 of the accompanying drawings is intended to be used in end-to-end nerve suture to eliminate tension between the nerve ends at the anastomosis site and thus allow optimal coaptation between these ends.

The element 1 comprises an elongated body 3 made of a material which is either rigid or slightly resilient and, of course, is biologically acceptable. Such a material is preferably a silicon resin like the one sold under the trademark SILASTIC, which is well known and commonly used in the medical art.

In accordance with the invention, the elongated body 3 is preferably made of a material that is slightly resilient enough to give some slack at the suture site between the nerve ends. This material must however not have too much resilience as it must actually act as a mechanical joint strong enough to transfer tension from the epineurium of one nerve end to the epineurium of the other nerve end while leaving the anastomosis site in-between tension free as will be explained in greater detail hereinafter. In this connection, it will be appreciated that the slight resiliency of the material makes is possible for the tension to be distributed substantially equally between all of the sutures. The slight resiliency also makes it possible to generate "artificially" some compression at the anastomosis site whenever this is necessary.

Figure 5:
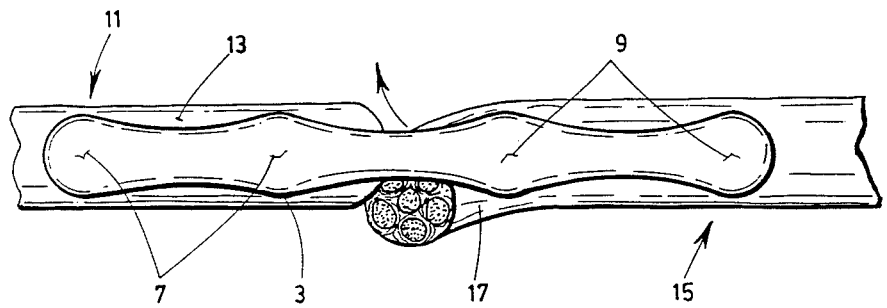
FIG. 5 appearing on the same sheets of drawings as FIGS. 1 to 3 is a side elevational view of the pair of nerve ends shown in FIG. 4, after suture of both of these ends to the splint-like elements but before anastomosis.
Figure 4:
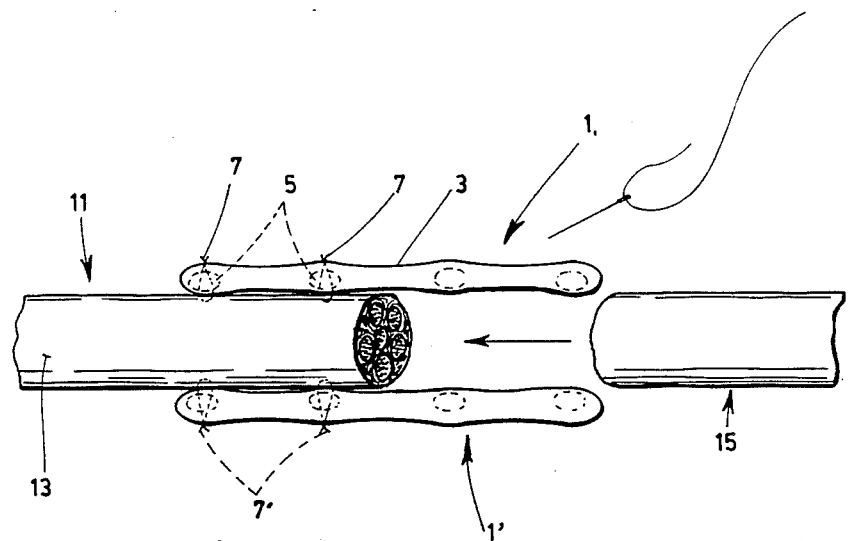
FIG. 4 is a top plan view of a pair of nerve ends to be sutured, with a pair of splint-like elements as shown in FIG. 1 symmetrically sutured onto one of the nerve ends.

The elongated body 3 may be of any shape provided however that it is elongated. It may also be of any length and/or diameter provided however that it is long enough to have one end attachable to the epineurium 13 of one of the nerve ends 11 to be sutured, by at least one but preferably two longitudinally spaced apart sutures 7, as shown in FIGS. 4 and 5. The elongated body 3 must also be long enough to have its other end attachable to the empinerium 17 of the other nerve end 15 to be sutured, also by at least one but preferably two other longitudinally spaced apart sutures 9 as shown in FIG. 5.

The splint-like element 1 also comprises pieces of reinforcing material placed along the body 3 wherever this body is intended to be attached by the sutures 7 and 9 to the epineurium of the nerve ends 11 and 15, respectively. The purpose of these pieces is essentially to provide mechanical "anchors" through which the suture wires may be passed and/or to which they may be attached, to prevent the elongated body 3 made of silicon resin or similar substance from being torn or otherwise cut by the sutures 7 and/or 9.

These pieces of reinforcing material may consist of patches of fabric embedded into the slightly resilient material of the elongated body 3. They may also consist of sheets of plastic material or metal fixed on top of the elongated body to be visible to the surgeon in charge of the nerve suture. Preferably however, these pieces consist of beads 5 of plastic material such as DACRON® embedded into the slightly resilient material, as shown in the drawings.

As aforesaid, the particular shape of the elongated body 1 is not an essential feature of the invention. It must however be understood that this shape must be as smooth as possible to avoid cutting or scratching of the surrounding tissues. As also aforesaid, the size, viz. the length and/or diameter of the elongated body 3 may substantially vary depending on the size of the nerve to be repaired and the amount of tension to eliminate at the anastomosis site. In most of the cases, two spaced apart sutures 7 or 9 made of 5-0 or 6-0 Nylon wires, will be sufficient to attach the element 1 to the epineurium of each nerve end in such a manner that any tension applied to one of the nerve ends is directly transferred to the other nerve end over a sufficient distance to leave the anastomosis site tension free. However, in some cases, like in cases of loss of nerve substance at the anastomosis site, damaged epineurium and/or potentially hightension at the anasotmosis site, use may be made of longer splint-like elements having opposite ends attachable by more than two spaced-apart sutures along the epineurium of each nerve end.

By way of example, the splint-like element 1 may be as long as 6 cm and have a diameter in-between the embedded beads 5 of up to 2 mm. For smaller nerves like those in the fingers, the element may be 1 cm long and 1 mm wide.

The splint-like element 1 disclosed hereinabove can be used as follows.

After preparation of the nerve ends to be sutured as is known in the medical art, a first splint-like element 1 as disclosed hereinabove may be attached by means of at least one but preferably two sutures 5 to one side of the epineurium 13 of one of the nerve ends. The sutures can be made with 5-0 or 6-0 Nylon suture wires to make the attachment strong enough to afford the tension that the nerve may undergo. As clearly shown in FIG. 4, only one end of the splint-like element 1 is attached to the epineurium 13 of the first nerve end 11 at the given distance from the anastomosis site. As also shown in FIG. 4, the attachment is carried out in such a manner that the other end of the element 1 projects from the one nerve end, away from the anastomosis site.

Then, a second splint-like element 1' is similarly attached by at least one but preferably two sutures 7' to the epineurium 13 of the first nerve end 11 at substantially the same given distance from the anastomosis site of the first element 1. This attachment is carried out in such a manner that the second element 1' extends parallel to the first element 1 on the opposite side of the nerve end 11, as clearly shown in FIG. 4.

Then, the other nerve end 15 may be pulled inbetween the free ends of the first and second splint-like elements 1 and 1' as shown with the arrow in FIG. 4. Such a pull must be carried out to such an extent that the free end of the other nerve end 15 be at least in contact with the free end of the one nerve end 11. However, it may advantageous under certain circumstance to pull the nerve end 15 to such an extent that it extend slightly over the one nerve 11, as will be explained hereinafter.

Then, the free ends of the first and second splint-like elements 1 and 1' may be attached to the epineurium 17 of the other nerve end 15 by means of at least one but preferably two further sutures 9, as shown in FIG. 5, thereby making the nerve suture site tension free.

Finally, both nerve ends 11 and 15 may be sutured according to any known technique to achieve the desired anastomosis. By way of example, such anastomosis can be made by wire suture, laser microanastomosis, adhesive microanastomosis, etc.

The advantages of pulling the other nerve end 15 to such an extent that it extends slightly over the one nerve end 11 are that, on the one hand, it makes it possible to create some "artificial" compression of the anastomosis site and that, on the other hand, it makes it possible to resect at least one but preferably two of the nerve ends 11 and 15 to adjust their length and shape to fit each other prior to suturing the fasciculi.

As can now be understood, reduction to practice of the present invention permits to distribute any tension symmetrically and uniformly on both sides of the anastomosis site onto the epineurium of the nerve. As a result, the anastlomasis site is left tension free and can even be held under compression.

Figure 6:
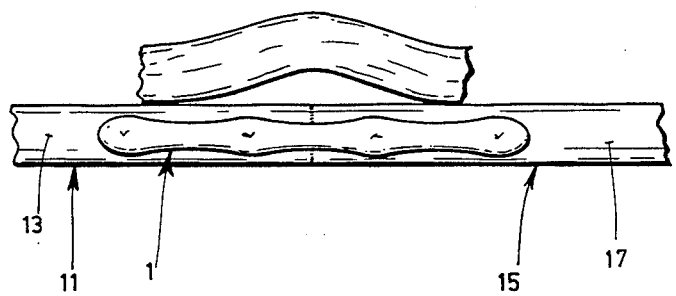
FIG. 6 is a view similar to the one of FIG. 5, showing a pair of nerve ends after suture and illustrating the way the splint-like elements according to the invention permit, under certain circumstances, avoiding the necessity of a nerve graft.

The main advantages that derive from such an elimination of the tension at the anastomosis site are as follows:

(1) the nerve fasciculi are much easier to orient and position;

(2) there is less fibrosis at the anastomosis site but much fibrosis around the nerve because of the presence of the splint-like elements;

(3) nerve grafting may be avoided in the case of a short or moderate lack of length in the nerve to be sutured (see FIG. 6 of the drawings).

(4) microanastomosis can be made safer; and (5) a compressive effect may be obtained whenever desired.

It is worth mentioning that, after a while, the splint-like elements 1 and 1' may be removed from around the nerve. However, such a removal is not compulsory.

It is also worth mentioning that, instead of using silicon resin or any similar material, use could also be made of a resorbable or biodegradable material to make the body 3, thereby making subsequent removal of the splint-like elements unnecessary.

What is claimed is:

1. A stent element for use in end-to-end nerve suture to eliminate tension between the nerve ends at an anastomosis site and thus allow optimal coaptation between said ends, said stent element comprising an elongated body made of a material that is slightly resilient and is biologically acceptable, said elongated body being long enough to have one end attachable to an epineurium of one of said nerve ends at a first given distance from the anastomosis site by at least one suture, and another end of said elongated body attachable to the epineurium of the other of said nerve ends at a second given distance from the anastomosis site by at least one other suture, said stent element further including pieces of reinforcing material consisting of beads of plastic material embedded into said slightly resilient material of said elongated body and disposed so as to prevent said elongated body from being torn or otherwise cut by said sutures.

2. The element of claim 1, wherein each of the ends of said elongated body comprises at least two beads of plastic material that are embedded into the slightly resilient material and longitudinally spaced apart to allow said body end to be attached to the epineurium of said nerve ends each by at least two sutures.

3. The element of claim 2, wherein said slightly resilient material is a silicone resin.

4. The element of claim 2, wherein said slightly resilient material consists of SILASTIC ® and said plastic material consists of DACRON ®.

5. A method of carrying out end-to-end nerve suture in order to achieve maximum coaptation between the nerve ends at the anastomosis site using stent elements provided with an elongated body made of a material that is slightly resilient and biologically acceptable, said method comprising the steps of:

attaching by means of at least one suture, one end of a first stent element to one side of the epineurium of one of said nerve ends to be sutured at a given distance from the anastomosis site in such a manner that the other end of said first element projects away from said one nerve end;

attaching by means of at least one other suture, the one end of a second stent element to the epineurium of said one nerve end at the same given distance from the anastomosis site in such a manner that said second element extends parallel to the first element on the opposite side of said one nerve end;

pulling the other of said nerve ends in between the other ends of said first and second stent elements to such an extent that said other nerve end be at least in contact with said one nerve end;

attaching each of said other ends of said first and second elements to the epineurium of said other nerve end by means of at least one further suture, thereby making the nerve suture site tension-free; and then suturing together both of said nerve ends to achieve anastomosis.

6. The method of claim 5, wherein said first and second stent elements further include beads of plastic material embedded into the elongated bodies as pieces of reinforcing material, to prevent said bodies from being torn or cut by the sutures.

7. The method of claim 5, wherein said first and second stent element further include at least two beads of plastic material embedded into each of their body ends, and wherein each of said body ends is attached to the epineurium of the corresponding nerve end by at least two sutures.

8. The method of claim 7 wherein said first and second stent element further include at least two beads of plastic material embedded into each of their body ends, and wherein each of said body ends is attached to the epineurium of the corresponding nerve end by at least two sutures.

9. The method of claim 7, wherein use is made of a 5-0 nylon suture wire to attach said first and second stent elements to said one nerve end and said other nerve end.

10. The method of claim 7, wherein use is made of a 6-0 nylon suture wire to attach said first and second stent elements to said one nerve end and said other nerve end.

11. The method of claim 5, wherein said nerve end is pulled in-between said first and second stent elements to such an extent that said other nerve end extends slightly over said one nerve end.

12. The method of claim 11, wherein said first and second stent elements further include beads of plastic material embedded into the elongated bodies as pieces of reinforcing material to prevent said bodies from being torn or cut by the sutures.

13. The method of claim 12, wherein said first and second stent element further include at least two beads of plastic material embedded into each of their body ends, and wherein each of said body ends is attached to the epineurium of the corresponding nerve end by at least two sutures.

14. The method of claim 11, comprising the additional step of resecting at least one of said nerve ends to adjust its length and shape to fit the other of said nerve ends prior to suturing both of said nerve ends.

15. The method of claim 14, wherein said first and second stent elements further include beads of plastic material embedded into the elongated bodies as pieces of reinforcing material to prevent said bodies from being torn or cut by the sutures.

16. The method of claim 5, wherein use is made of a 5-0 nylon suture wire to attach said first and second stent elements to said one nerve end and said other nerve end.

17. The method of claim 5, wherein use is made of a 6-0 nylon suture wire to attach said first and second stent elements to said one nerve end and said other nerve end.

* * * * *